United States Patent [19]

Jarreau et al.

[11] 4,219,549
[45] Aug. 26, 1980

[54] AMINO-3 CARDENOLIDES, PROCESS FOR PREPARATION, AND PHARMACEUTICAL COMPOSITIONS CONTAINING SAME

[75] Inventors: Francois X. Jarreau, Versailles; Jean J. Koenig, Chilly-Mazarin, both of France

[73] Assignee: Etablissements Nativelle S.A., Paris, France

[21] Appl. No.: 6,709

[22] Filed: Jan. 26, 1979

[30] Foreign Application Priority Data

Jan. 27, 1978 [FR] France .................... 78 02391

[51] Int. Cl.$^2$ .................................................. C07J 19/00
[52] U.S. Cl. ................................. 424/241; 260/239.57
[58] Field of Search .................. 260/239.57; 424/241

[56] References Cited

U.S. PATENT DOCUMENTS

| | | | |
|---|---|---|---|
| 3,725,393 | 4/1973 | Stache et al. | 260/239.57 |
| 3,801,576 | 4/1974 | Stache et al. | 260/239.57 |
| 4,060,607 | 11/1977 | Jarreau et al. | 424/241 |

*Primary Examiner*—Elbert L. Roberts
*Attorney, Agent, or Firm*—Sughrue, Rothwell, Mion, Zinn and Macpeak

[57] ABSTRACT

Aminocardenolides of formula (I):

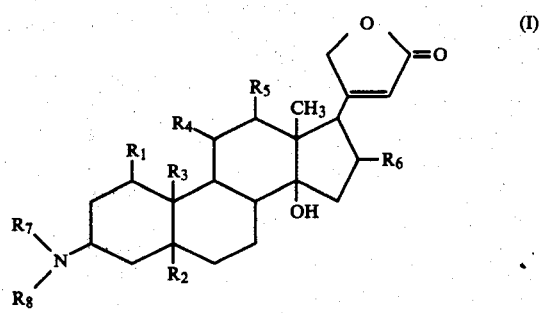

in which $R_1$, $R_2$, $R_4$, $R_5$, and $R_6$, which may be the same or different, each represents a hydrogen atom or a hydroxy, alkoxy or acyloxy group; $R_3$ represents a lower alkyl, hydroxyalkyl, acyloxyalkyl, haloalkyl or ethylenedioxyalkyl group; $R_7$ represents a hydrogen atom, or an alkyl or acyl group, and $R_8$ represents a hydrogen atom, an alkyl group or an amino acid residue; a process for preparation of the compounds with the above formula by reaction of an oxo-3 genin with an ammonium salt in the presence of a borocyanohydride in an organic solvent. The aminocardenolides of formula (I) are useful especially for the treatment of cardiac ailments.

14 Claims, No Drawings

AMINO-3 CARDENOLIDES, PROCESS FOR PREPARATION, AND PHARMACEUTICAL COMPOSITIONS CONTAINING SAME

BACKGROUND OF THE INVENTION

1. Field Of The Invention

The present invention relates to derivatives of aminocardenolides, to a process for their preparation and their therapeutic applications.

2. Description Of The Prior Art

It is well known that numerous natural substances derived from cardiotonic heterosides are used therapeutically for the treatment of cardiac disorders. The cardiotonic activity of the cardenolide-glycosides, especially, depends principally on the structure of the cardenolide part and on the nature of the sugar-containing chain attached at $3\beta$. Because of the low therapeutic activity of these natural substances, and the disadvantages which occur from their utilization, it seemed interesting to prepare compositions of similar structure possessing satisfactory cardiotonic activity together with low toxicity.

It was suggested that an appropriate substituent be attached in the 3 position of the cardenolide moiety, preferably at $3\beta$ position. For example, French Pat. Nos. 2,085,722 and 2,111,705 describe cardenolide derivatives substituted at the $3\alpha$ and $3\beta$ positions by an amino or alkylamino group.

However, the preparation of such compositions, containing a substituent attached by a nitrogen atom at the 3 position of the cardenolide, becomes all the more difficult and delicate as the substituent is complex and itself comprises one or more functional groups. The preparation of such compositions must then be carried out in several steps, and it is necessary first of all to prepare the derivative of cardenolide substituted at the 3 position by an NH$_2$ group, for example, by the action of hydroxylamine on an oxo-3 cardenolide to form an oxime which is reduced by hydrogen in the presence of a metallic catalyst. A primary amine can also be used to form a Schiff base which is then catalytically hydrogenated. This amino-3 cardenolide can then be used as an intermediate for the preparation of other compositions with substitution on the nitrogen atom.

These processes are difficult to bring about because of the large number of steps which they require and of the fragility of the cardenolide moiety, especially the lactone ring attached at the 17 position, of which saturation must be avoided by carefully monitoring the reduction step.

SUMMARY OF THE INVENTION

The present invention provides a new process which enables the preparation of various compositions of the amino-3 cardenolide type in one step, with good yield, and avoiding the above-noted disadvantages. More especially, the process according to the invention enables amino groups, both primary, secondary and tertiary, possibly functional, to be obtained at the 3 position of the cardenolide, in a single step starting from an oxo-3 genin, without reducing the lactone ring of the cardenolide.

The present invention also provides new cardenolide derivative compounds substituted at the 3 position by a group of the functional amino group type, as well as the therapeutic application of the same especially for cardiac ailments and rhythm problems.

Accordingly, in one embodiment, this invention provides a process for producing cardenolide derivatives represented by the formula (I):

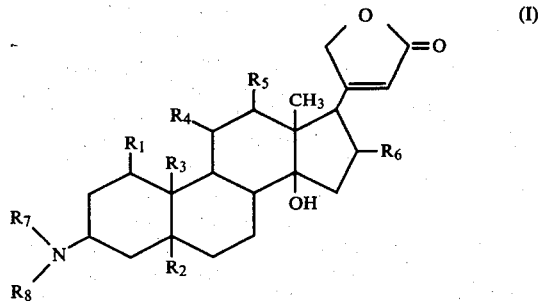

comprising reacting an oxo-3 genin, such as digitoxigenone or digoxigenone, with an ammonium salt in the presence of a borocyanohydride, in an organic solvent, such as an alcohol, in which $R_1$, $R_2$, $R_4$, $R_5$, and $R_6$, which may be the same or different, each represents a hydrogen atom or a hydroxy, alkoxy or acyloxy group; $R_3$ represents a lower alkyl, hydroxyalkyl, acyloxyalkyl, haloalkyl or ethylenedioxyalkyl group; $R_7$ represents a hydrogen atom, an alkyl or an acyl group; and $R_8$ represents a hydrogen atom, an alkyl group or an amino acid residue.

Also, this invention in another embodiment provides compounds obtained in accordance with the above-described process, by attaching to the cardenolide, at the $3\alpha$ or $3\beta$ position, a functional amino group; in particular derivatives of the alkylamino-3 cardenolide type represented by the following general formula (II):

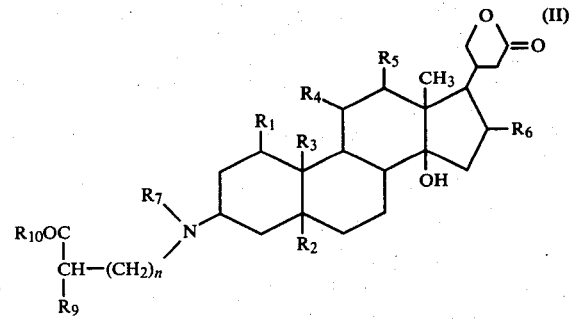

wherein $R_1$ to $R_7$ have the definitions as given for the Formula (I); $R_9$ represents a hydrogen atom, an alkyl group or —NR$_{11}$R$_{12}$, where R$_{11}$ and R$_{12}$, which may be the same or different, each represents a hydrogen atom, or an alkyl or aryloxycarbonyl group; R$_{10}$ represents a hydroxy, alkoxy, aryloxy or aralkoxycarbonyloxy group; and n is an integer from 0 to 6.

DETAILED DESCRIPTION OF THE INVENTION

As a cardenolide starting material, oxo-3 cardenolides which are easily obtained from the corresponding genins in the $3\alpha$ or $3\beta$ forms, using classical methods, can be chosen and more especially 3-digitoxigenone, 3-digoxigenone, oxo-3 acetoxy-12$\beta$ digoxigenin, uzarigenone, etc. are suitable.

An ammonium salt, corresponding to the amino substituent which it is wished to introduce at 3α or 3β, is contacted with these oxo-3 cardenolides. For example, ammonium acetate, methylamine hydrochloride, dimethylamine hydrochloride, or a salt of a monoamino or diamino acid such as glycine, taurine, alanine, leucine, lysine, ornithine or diaminobutyric acid, or an amine salt of an oligo-peptide can be used.

Under these conditions an immonium intermediate is formed, within the reaction medium, which is reduced to amino-3 cardenolide in the presence of a borocyanohydride of an alkali metal, following a reaction analogous to that described by Borch et al *J. Am. Chem. Soc.*, 93, 2897 (1971). The reaction is advantageously conducted in the presence of sodium or potassium borocyanohydride, in various solvents such as alcohols, for example, methanol or isopropanol, or water and acetonitrile.

The process of the present invention takes place under normal pressure, at a temperature of between 0° and 40° C., and preferably at room temperature.

According to a preferred embodiment of the process of the present invention, a solution is made in methanol or isopropanol of oxo-3 cardenolide and an appropriate ammonium salt, then sodium borocyanohydride is added, at ordinary temperature during stirring. The stirring is continued throughout the period of reaction, then the solvent is distilled off under reduced pressure. The amino-3 cardenolide thus formed is then extracted and purified in accordance with normal techniques.

Among the compositions represented by Formula (II) above, preferred compositions are those in which $R_1$, $R_2$, and $R_6$ represent a hydrogen atom or a hydroxy group, $R_3$ represents a lower alkyl group, for example, a methyl group, or a hydroxyalkyl group, for example a hydroxymethyl group, or an aldehyde group; $R_4$ represents a hydrogen atom; and $R_5$ represents a hydrogen atom, a hydroxy group or an acetoxy group.

This invention provides particular derivatives of amino-3 cardenolides and of amino acids and preferably the following compounds as well as the salts thereof:

Compound A—deoxy-3 ε-L-lysylamino-3α digitoxigenin

Compound B—deoxy-3 ε-L-lysylamino-3β digitoxigenin

Compound C—deoxy-3 N-(ε-L-lysyl) N'-acetylamino-3α digitoxigenin

Compound D—deoxy-3 N-(ε-L-lysyl) N'-acetylamino-3β digitoxigenin

Compound E—deoxy-3 ε-L-lysylamino-3α acetoxy-12β digoxigenin

Compound F—deoxy-3 ε-L-lysylamino-3β acetoxy-12β digoxigenin

Compound G—deoxy-3 N-glycylamino-3α digitoxigenin

Compound H—deoxy-3 N-glycylamino-3β digitoxigenin

The compositions of the Formula (II) in accordance with the present invention have the advantage that their molecule includes both a —$COR_{10}$ acid group and a basic amino group which enables their transformation in the form of salts by the action of bases or mineral or organic acids.

The invention also includes the salts of the amino-3 cardenolide derivatives, in particular the pharmaceutically acceptable salts, by reaction with usual acids, such as hydrochloric, sulfuric, phosphoric, acetic, propionic, oxalic, lactic, citric, tartaric, ascorbic, aspartic, glutamic, or malonic acids, or with an alkali metal hydroxide, for example, sodium, potassium or lithium hydroxide, or an alkaline earth metal hydroxide, such as magnesium or calcium hydroxide. Metal salts, such as aluminum, or ammonium salts can also be prepared.

The salts can be obtained in the usual manner, by reacting substantially stoichiometric proportions of the amino-3 cardenolide derivative in the form of the free acid or the free base with an appropriate acid or hydroxide in a solvent suitably chosen in terms of the acid or the base, for example, water or an alcohol.

The above-described amino-3 cardenolide derivatives are obtained in accordance with the process of the present invention in the form of a mixture of their 3α and 3β isomers. These isomers can be separated by classical methods, for example by chromatography or by crystallization of their respective salts.

Pharmacological and toxicological evaluations carried out on the amino-3 cardenolide derivatives and their salts have shown evidence of interesting properties enabling their therapeutic application.

The compounds of the present invention show, in effect, a cardiotonic action similar to that of known cardiotonic heterosides, with a better therapeutic margin, i.e., a larger interval between an active dose and a toxic dose.

Thus, it has been observed that the amino-3 cardenolide derivatives of the present invention show inhibitive activity of $Na^+$ on dependent ATPase $Na^+$, $K^+$, significant of activity of digitalic compounds, verified on rat brain tissue.

The similarity between the action of compounds of the present invention and those of known cardiotonic heterosides has been confirmed by inotropic activity verified on the isolated and perfused (Langendorf) heart of a guinea pig and in situ on dog heart.

The compounds of the present invention are moreover characterized by persistence in inhibitive activity on membraneous ATPase, while, to the contrary, inotropic activity varies in accordance with the nature of the substituent attached to the nitrogen atom in the 3 position and in accordance with the starting cardenolide itself. It has been observed, for example, that for the above-mentioned compounds the percentages of inhibition of the dependent membranous ATPase of guinea pig brain, for dozes of enzymatic protein of 36 μg/mg and 0.36 μg/mg, are largely equivalent to those of digoxin and digitoxin.

These pharmacological properties comparable to those of known cardiotonic heterosides, in spite of the presence of a peptide residue at the 3 position of the steroid ring, in the place of the heteroside sugars, show that the amino-3 cardenolide derivatives of the present invention can be utilized for treatment of cardiac affections and in particular cardiac insufficiency and rhythm troubles.

The new compounds of the present invention can be administered in the usual forms containing a pharmacologically effective amount of the compound as an active ingredient in pharmaceutically acceptable supports, for example, in the form of tablets, gelules, capsules, pills, suppositories, injectable solutions or syrups.

As a solid diluant for the preparation of tablets, lactose, mannitol, sorbitol, starch, polyvinylpyrrolidone, magnesium or aluminum stearate, cellulose powder, colloidal silica, talc, etc. may be used.

Injectable solutions may be prepared using diluants such as double distilled water, propylene glycol, a hydroalcoholic solution, or a mixture of these diluants, preferably in the presence of a suitable preservative selected from those used normally in the art.

Orally ingestible forms can also be prepared, for example, solutions containing the compounds of the present invention dissolved in water and glycerol in the presence of a sweetening agent and an antioxidant, or suspensions of the composition of the present invention in an aqueous solution of saccharose in the presence of a thickener, a sweetening agent and an antioxidant.

All formulations adapted to various types of administration, i.e., orally, parenterally, or rectally, can be used, the compound being present as the therapeutically active ingredient with suitably selected acceptable pharmaceutical excipients.

For example, the following formulations may be cited:

Tablets:

| A- | Compound B | 0.25 | mg |
| | Lactose | 134.75 | |
| | Talc | 15.0 | |
| | | 150.0 | mg |
| B- | Compound F | 0.25 | mg |
| | Starch | 81.25 | |
| | Colloidal Silica | 0.50 | |
| | Microcrystalline Cellulose | 18.00 | |
| | | 100.0 | mg |
| Injectable Solution: | | | |
| | Compound B | 0.01 | mg |
| | Preservative | 0.001 | |
| | Water (quantity sufficient for) | 1.0 | ml |
| Oral Suspension: | | | |
| | Compound F | 0.25 | g |
| | Thickener | 10.0 | g |
| | Saccharose | 25.0 | g |
| | Sweetening Agent | 1.0 | g |
| | Antioxidant | 0.0001 | g |
| | Water (quantity sufficient for) | 100.0 | ml |

The dosage may vary in accordance with the subject being treated and the affliction in question, the doses administered daily being generally on the order of between 0.01 and 1 mg for oral administration in man.

The formulation examples described above are merely illustrative and not limitative of the scope of the invention.

EXAMPLE 1

Deoxy-3 amino-3 digitoxigenin

A solution of 484 mg of 3-digitoxigenone and 770 mg of ammonium acetate in 50 ml of propanol-2 was agitated for 30 minutes at room temperature. 96 mg of sodium borocyanohydride was added and allowed to react under agitation for 30 minutes.

The solvent was evaporated to dryness and the residue was dissolved in 50 ml of 1 N hydrochloric acid. After extraction with ethyl acetate, the organic phases were twice washed with 25 ml of 1 N hydrochloric acid, then with water, finally with solutions of sodium bicarbonate and sodium chloride, then they were dried and evaporated to dryness. The residue (55 mg) was composed of several products of low polarity in which there were traces of the starting ketone, but without traces of $3\alpha$ or $3\beta$ digitoxigenin (determination by TLC: Kieselgel Merck; eluent: $CH_2Cl_2 + MeOH$ (2.5%) ammonia atmosphere).

The acid phases, combined and rendered alkaline with ammonia, were extracted with methylene chloride. The extract was washed, dried and evaporated to dryness. The residue (370 mg) was composed of a mixture of amino-$3\alpha$ and $3\beta$ digitoxigenin isomers (yield=77%).

300 mg of this residue was dissolved in 5 ml of methanol at reflux. 110 mg of oxalic acid as a solution in 5 ml of methanol was added incrementally. The residue was distilled to dryness and crystallized first in the ethanol/ethyl acetate mixture and a second time in pure ethanol. The oxalate crystals obtained in an ammoniacal medium were reextracted with methylene chloride. The extract was washed, dried and evaporated to dryness to obtain 65 mg of deoxy-3 amino-$3\beta$ digitoxigenin residue (yield=17%).

The physical constants (m.p., TLC, IR and NMR) are identical to those of the product described in the literature.

EXAMPLE 2

Deoxy-3 acetylamino-3 digitoxigenin

A solution of 66 mg of the mixture of the $3\alpha$ and $3\beta$ isomers of deoxy-3 amino-3 digitoxigenin in 1 ml of pyridine and 0.5 ml of acetic anhydride was left for 1 hour at ordinary temperature. The mixture was thrown into ice water, acidified with hydrochloric acid to a pH of 3-4 and extracted with methylene chloride. The extract was washed, dried and evaporated to dryness. The residue (73 mg) was composed of a mixture of the acetylamino-$3\alpha$ and $3\beta$ digitoxigenin isomers (yield=100%).

The NMR spectrum ($CDCl_3$) showed that the relationship of the $3\alpha$ and $3\beta$ isomers obtained was on the order of 3/2.

By the same process, starting with amino-$3\beta$ digitoxigenin, deoxy-3 acetylamino-$3\beta$ digitoxigenin was obtained.

EXAMPLE 3

Deoxy-3 N-dimethylamino-digitoxigenin

A solution of 484 mg of 3-digitoxigenone and 810 mg of dimethylamine hydrochloride in 50 ml of propanol-2 was agitated at ordinary temperature for 1 hour. 96 mg of sodium borocyanohydride was added and allowed to react for 20 hours. The solvent was evaporated off and the residue was dissolved in 50 ml of 1 N hydrochloric acid. After extraction with ethyl acetate, the organic phase was washed with 1 N hydrochloric acid, water and solutions of sodium bicarbonate and sodium chloride. Then it was dried and evaporated to dryness.

The residue (148 mg) was composed of the starting ketone and of $3\alpha$ and $3\beta$ digitoxigenin (determination by TLC). The acid phases were combined and rendered alkaline with ammonia and then extracted using methylene chloride. The extract was washed, dried and evaporated to dryness. The residue (311 mg) was composed of the $3\alpha$ and $3\beta$ isomers of deoxy-3 N-dimethylamino-3 digitoxigenin (yield=60%).

The two isomers were separated on a preparation plate (Merck, 60 F silica gel, thickness 2 mm). By using as an eluent a methylene-methanol chloride mixture (97.5/2.5) in an atmosphere saturated with ammonia, the deoxy-3 N-dimethylamino-$3\beta$ digitoxigenin (44%) was extracted from the least polar strip and deoxy-3 N-methylamino-3 digitoxigenin (56%) from the most polar strip.

Analysis of these products gave the following results, which conform to those of the literature:

Deoxy-3 N-dimethylamino-3β digitoxigenin

Hydrochloride
m.p. (Kofler): 258°–260° C. dec.
Free base
m.p. (Kofler): 216°–220° C.
IR spectrum (Nujol: 3340, 2810, 2765, 2715, 2680, 1775, 1740 1630 and 1615 cm$^{-1}$
TLC eluent: CH$_2$Cl$_2$—MeOH, (97.5/2.5, atmosphere saturated with NH$_3$)
Indicator: I$_2$
Rf=0.63

Deoxy-3 N-dimethylamino-3α digitoxigenin

IR spectrum (Nujol): 3450, 2810, 2770, 1780, 1745, 1620 cm$^{-1}$
TLC: Rf=0.5

EXAMPLE 4

Deoxy-3 N-methylamino-3 digitoxigenin 250 mg of sodium borocyanohydride was added to a solution of 2 g of digitoxigenone and 3 g of methylamine hydrochloride in 50 ml of methanol.

The mixture was agitated for 5 hours at room temperature, then flooded with water, acidified with hydrochloric acid, washed with methylene chloride, rendered alkaline with ammonia and extracted with methylene chloride. The organic extract was washed, dried and evaporated to dryness, then the residue was chromatographed on a column of 150 g of standardized aluminate (I–III) in accordance with Brockmann Merck. From fractions eluted with a mixture of methylene chloride and methanol (99.5/0.5) 717 mg of a white monospot residue of deoxy-3 N-methylamino-3β digitoxigenin was isolated. The fractions eluted with a methylene chloride-methanol mixture (98/2) gave 630 mg of deoxy-3 methylamino-3α digitoxigenin.

3β-base isomer:

The extraction of 177 mg of the hydrochloride of the 3β isomer in ammoniacal medium using methylene chloride gave after washing, drying and evaporation to dryness of the extract a residue of 162 mg of deoxy-3 methylamino-3β digitoxigenin.

Deoxy-3 methylamino-3β digitoxigenin

IR spectrum (Nujol): 3490, 3330, 2775, 1780, 1730 and 1613 cm$^{-1}$
NMR spectrum (CDCl$_3$): w=0.86 0.94 and 2.34 (3s, CH$_3$) 2,5 to 2.9 (2H+NH) 4.88 (2H) 5.80 (1H) ppm.
TLC: (CH$_2$Cl$_2$—MeOH, 97.5–2.5), Rf=0.36 (Indicator: I$_2$)
Hydrochloride m.p.=270° C. dec. (methanol—acetone)

EXAMPLE 5

Deoxy-3 N-methyl,N-acetyl amino-3β digitoxigenin 150 mg of the 3β isomer obtained in Example 4 was left to react in a solution of 6 ml of anhydrous methanol and 1.5 ml of acetic anhydride for 4 hours at room temperature.

The medium was concentrated in a vacuum, the residue flooded in water, rendered alkaline with sodium bicarbonate and extracted with methylene chloride. The extract was washed, dried and evaporated to dryness. The residue (159 mg) was crystallized in an acetone-ether mixture. 142 mg of pure deoxy-3 N-methyl,N-acetylamino-3β digitoxigenin crystals was obtained (yield=85%).
m.p. Kofler: 228°–230° C.
IR (Nujol): 3405, 1778, 1745, 1629 and 1608 cm$^{-1}$
NMR (CDCl$_3$): w=0.88, 0.97 2.08 and 2.93 (4s, CH$_3$), 2.80 (1H), 4.92 (2H), 5.85 (1H) ppm.
TLC: (CH$_2$Cl$_2$—MeOH, 90/10) Rf=0.5 (indication by I$_2$).

By proceeding in the same manner starting with the 3α isomer, deoxy-3 N-methyl,N-acetylamino-3α digitoxigenin was obtained.
m.p. (Kofler): 190°–192° C.
IR (Nujol): 3405, 1790, 1748, 1718 and 1620 cm$^{-1}$.

EXAMPLE 6

Deoxy-3 N-W(benzyloxy butyrate) amino-3digitoxigenin (3α and 3β isomers)

416 mg of digitoxigenenone and 1.058 g of the tosylate of the benzyl ester of γ-amino butyric acid were agitated for 45 minutes at room temperature in 10 ml of propanol-2. 90 mg of sodium borocyanohydride and 10 ml of propanol-2 were added. After 72 hours of agitation at room temperature, it was evaporated to dryness, flooded with water, rendered alkaline with sodium bicarbonate and extracted with methylene chloride. The extracts washed, dried and evaporated to dryness gave 797 mg of residue.

This residue was dissolved in 10 ml of boiling tetrahydrofuran (THF) to which had been added 145 mg of oxalic acid in 5 ml of boiling THF. After precipitation by the addition of ether, the insoluble material was filtered and crystallized in water.

The crystals were dissolved in dilute ammonia. Extraction was performed with methylene chloride and the extracts washed, dried and evaporated to dryness gave 180 mg of the 3β isomer in the form of an oil.

All the mother liquor (THF) was evaporated to dryness, dissolved in propanol-2, and the remaining 3β isomer was removed by cold filtration (20 mg). After evaporating to dryness, the filtrate was dissolved in 1 N hydrochloric acid and washed with ethyl acetate. The organic fractions were reextracted with dilute hydrochloric acid.

After rendering the hydrochloric fractions alkaline with ammonia and extraction with methylene chloride, the organic phases were washed, dried and evaporated to dryness. The residue, 112 mg contained almost exclusively the 3α isomer in the form of an oil.

The fractions of ethyl acetate, washed, dried and evaporated to dryness gave 169 mg of a residue containing 50% of the α-isomer and a more polar product.
Isomer 3α C$_{34}$H$_{47}$O$_5$N, M=549.72
IR (film): ν=3450, 2030, 1775, 1740, 1665, 1620, 1500, 1170, 1028 cm$^{-1}$
TLC (CH$_2$Cl$_2$—MeOH, 99/1, NH$_3$ atmosphere) Rf=0.28
Isomer 3β:
IR (film): ν=3470, 3018, 1780, 1745, 1730, 1670, 1620, 1500, 1165, 1028 cm$^{-1}$
TLC: (CH$_2$Cl$_2$—MeOH, 99/1, NH$_3$ atmosphere) Rf=0.33.

EXAMPLE 7

Deoxy-3 N-ω butyryl-amino-3α digitoxigenin.

75 mg of the 3α isomer obtained in Example 6 was hydrogenated in a solution of 15 ml of methanol, in the presence of 20 mg of palladium at 5% on calcium carbonate, for 28 hours. After filtration and evaporating the filtrate to dryness, the residue (68 mg) was crystallized in ethyl acetate. Thus, 37 mg of deoxy-3 N-ω butyrylamino-3α digitoxigenin crystals was obtained (yield=61%).

$C_{27}H_{41}O_5N$, M=459.60 m.p. (Kofler)=168-175 (dec)° C.

IR spectrum (Nujol) v=3410, 1780, 1740, 1621, 1565, 1200, 1175, 1025 cm$^{-1}$.

NMR spectrum (CDCl$_3$+CD$_3$OD) δ=0.86 and 0.95 (2s, CH$_3$) 2,41 (2H) 2.7-3.5 (3H), 5.0 (2H) 5.90 (s, 1H) ppm.

TLC (CHCl$_3$—EtOH—NH$_4$OH, 50/45/15) Rf=0.54.

By proceeding in the same manner starting with the 3β isomer obtained in Example 6, deoxy-3 N-ω butyrylamino-3β digitoxigenin was obtained.

m.p. (Kofler)=185°-195° C. (dec)

IR spectrum (Nujol) v=3380, 2530, 1680, 1740, 1720, 1625, 1520, 1270, 1030 cm$^{-1}$.

EXAMPLE 8

Deoxy-3 N-ω(benzyloxy glycinate)amino-3 digitoxigenin (3α and 3β isomers)

320 mg of digitoxigenone and 625 mg of O-benzyl glycine tosylate were agitated for 30 minutes at room temperature in 10 ml of propanol-2. 70 mg of sodium borocyanohydride was added.

After 4 hours of agitation at room temperature, it was evaporated to dryness and the residue was dissolved in water. It was rendered alkaline with sodium bicarbonate, extracted with ethyl acetate to obtain, after evaporation to dryness, 601 mg of residue. This was dissolved in 10 ml of boiling THF and then 230 mg of oxalic acid was added to the boiling THF. After cold crystallization, filtration of the crystals, which were dissolved in diluted ammonia, extraction with ethyl acetate was conducted. The extract washed, dried and evaporated to dryness gave 143 mg of the 3β isomer in the form of an oil (yield=31%).

The mother liquor was evaporated to dryness and the residue was dissolved in dilute ammonia and extracted with ethyl acetate. The extract washed, dried and evaporated to dryness gave 293 mg of the impure 3α isomer, in the form of an oil (yield=65%).

Isomer 3α $C_{32}H_{43}O_5N$, M=521.66

IR (film) v=3450, 3020, 1780, 1740, 1660, 1620, 1500, 1170, 1028 cm$^{-1}$.

TLC (CH$_2$Cl$_2$—MeOH, 90/10) Rf=0.75

Isomer 3β

IR (film) v=3460, 3340, 3020, 1785, 1745, 1670, 1622, 1500, 1180, 1028 cm$^{-1}$ NMR (CDCl$_3$) δ=0.88 and 0.93 (2s, CH$_3$), 2.85 (1H), 3.0 (1H), 3,55 (2H), 5.1 (2H), 5.33 (2H), 6.08 (1H) 7.6 (5H) ppm.

TLC (CH$_2$Cl$_2$—MeOH, 90/10) Rf.=0.80.

EXAMPLE 9

Deoxy-3 N-glycyl amino-3α digitoxigenin.

150 mg of the 3α isomer obtained in Example 8 was hydrogenated in a solution of 15 ml of methanol, in the presence of 30 mg of palladium at 5% on calcium carbonate, for 20 hours. This was filtered and the filtrate was evaporated to dryness. After purification of the residue (115 mg) by washing in ethyl acetate and trituration in ether, 90 mg of deoxy-3 N-glycylamino-3α digitoxigenin was thus obtained. (yield=75%).

$C_{25}H_{35}O_5N$, M=429.53 m.p. (Kofler)=195°-210° C. (dec.)

TLC (CHCl$_3$—EtOH—NH$_4$OH, 50/45/15) Rf=0.51.

By proceeding in the same manner starting with 110 mg of the β isomer obtained in Example 8, 88 mg of deoxy-3 N-glycylamino-3β digitoxigenin crystals was obtained (yield=76%).

m.p. (Kofler): 225°-230° C. (dec)

IR (Nujol) v=3530, 3400, 1788, 1758, 1720, 1625, 1598 and 1034 cm$^{-1}$.

NMR (CDCl$_3$+CD$_3$OD) δ=0.88 and 1.03 (2s, CH$_3$), 2.83 (1H) 3.46 (2H), 3.1-3.7 (1H), 4.98 (2H) 5.91 (1H) ppm.

TLC (CHCl$_3$—EtOH—NH$_4$OH, 50/45/15) Rf=0.53

EXAMPLE 10

Deoxy-3 ε-(α-N-benzyloxycarbonyl O-benzyl)-(L)-lysylamino-3 digitoxigenin 0.32 g of sodium borocyanohydride was added under agitation and at room temperature to 1.48 g of 3-digitoxigenone and 3.43 g of α-N-benzyloxycarbonyl O-benzyl-(L)-lysine benzenesulfonate in solution in 50 ml of methanol. After agitation for 6 hours, the methanol was evaporated off under reduced pressure, and the residue was dissolved in 100 ml of a solution saturated with sodium bicarbonate. This was extracted with methylene chloride. It was washed, dried and evaporated to dryness and then the residue (4.15 g) was dissolved in 100 ml of ethyl acetate. After washing with 1 N hydrochloric acid, water, a solution saturated with sodium bicarbonate, and finally with water, it was reextracted in the same manner with ethyl acetate. The organic fractions were dried and evaporated to dryness and a residue (3.27 g) composed of a mixture of 3α and 3β still containing amino acid was obtained. This was dissolved in 10 ml of methanol and was added drop by drop to 0.54 g of oxalic acid in a solution of 10 ml of methanol at reflux. The residue was crystallized in ethyl acetate containing a little ether. The first product (1.07 g composed of the oxalate of the least polar product) was recrystallized in ethyl acetate and the base was liberated by dissolution in water, rendering alkaline and extraction with chloroform. After drying and evaporation, 0.88 g was obtained of the least polar product which is the 3β isomer of deoxy-3[ε-(α-N-benzyloxycarbonyl O-benzyl-L-lysyl]-amino-3 digitoxigenin (yield=30%).

The second product mother liquors were evaporated to dryness, the residue (2.3 g composed essentially of the oxalate of the most polar product) was washed with ether and the base was liberated. After washing with toluene, 152 g of an oil which was the 3α isomer of deoxy-3[ε-(α-N-benzyloxycarbonyl, O-benzyl-L-lysyl-]amino-3 digitoxigenin was obtained (yield=53%).

3β Isomer m.p. (Kofler) (oxalate)=191°-192° C.

IR spectrum (Nujol): 3450, 3340, 1780, 1745, 1725, 1620, 1530 cm$^{-1}$.

NMR spectrum (CDCl$_3$) δ=0.85 and 0.95 (2s, CH$_3$), 2.60 (3H) 2.99 (s, 1H), 4.35 (1H), 4 to 4.7 (NH and OH), 4.85 (2H), 5.05 and 5.10 (2s, CH$_2$), 5.52 (NH, d, J=7), 5.80 (s, 1H), 7.30 (s, 10H)ppm.

3α Isomer

IR (Nujol): 3440, 3340, 1780, 1740, 1715, 1620, 1530 cm$^{-1}$.

TLC: CH$_2$Cl$_2$—MeOH, 99/1, NH$_3$ atmosphere

3α isomer Rf=0.48

3β isomer Rf=0.54.

EXAMPLE 11

Deoxy-3 N-ε-(α-N-benzyloxycarbonyl O-benzyl)-(L)-lysyl N'-acetylamino-3 digitoxigenin (a) 3β isomer 400 mg of the 3β isomer obtained as indicated in Example 10 was placed in solution in 2.5 ml of acetic anhydride and 5 ml of pyridine and left to react for 3 hours at room temperature. At the end of the reaction it was poured on to ice water, acidified to a pH 2-3 with hydrochloric acid and then extracted with methylene chloride; the organic fractions were washed with sodium bicarbonate, then with water, dried and evaporated to dryness. The residue was composed of 420 mg of deoxy-3 N-ε(α-N-benzyloxycarbonyl O-benzyl)-(L)-lysyl N'-acetylamino-3β digitoxigenin (yield: 98%).

IR spectrum (Nujol): 3430, 3340, 1755, 1745, 1720, 1620 and 1530 cm$^{-1}$.

TLC ($CH_2Cl_2$—MeOH 95/5) Rf=0.28.

(b) 3α isomer

Starting with 760 mg of the 3α isomer produced in Example 10, and after extraction the residue (779 mg) was chromatographed on 40 g of Merck 40 silica. The fractions eluted with a methylene chloride-methanol mixture (98/2) gave 400 mg of deoxy-3 N-ε-(α-N-benzyloxycarbonyl O-benzyl)-(L)-lysyl N'-acetylamino-3α digitoxigenin (yield=50%).

TLC: $CH_2Cl_2$—MeOH 95/5) Rf=0.27.

EXAMPLE 12

Deoxy-3 ε-(L)-lysylamino-3 digitoxigenin (a) 3α isomer 850 mg of the 3α isomer produced in Example 10 was dissolved in 85 ml of methanol and was hydrogenated in the presence of 210 mg of palladium at 5% on calcium carbonate for 6 hours. After filtration and evaporation to dryness, the residue (662 mg) was washed with chloroform, then triturated in a mixture of ethyl acetate and isopropyl ether. From this, 323 mg of a yellow crystalline insoluble material composed of deoxy-3 ε-(L)-lysylamino-3α digitoxigenin, Compound A, was obtained (yield=47%).

m.p. (Kofler) 190°-200° C. dec.

IR spectrum (Nujol): 3400, 1780, 1755, 1745, 1720, 1620 cm$^{-1}$.

NMR spectrum (CD$_3$OD): δ=0.87 and 0.95 (2s, CH$_3$), 2.97 (3H), 3.37 (1H), 4.05 (1H), 5.85 (s, 1H) ppm.

TLC (CHCl$_3$—EtOH—NH$_4$OH, 50/45/15) Rf=0.17.

(b) 3β isomer 439 mg of the 3β isomer obtained in Example 10 were dissolved in 40 ml of methanol and hydrogenated in the presence of 110 mg of palladium at 5% on calcium carbonate for 3.5 hours. After filtration and evaporation of the solvent to dryness the residue (336 mg) was crystallized in propanol-2. This gave 252 mg of deoxy-3 ε-(L)-lysylamino-3β digitoxigenin crystals, Compound B (yield=83%).

m.p. (Kofler) 185°-195° C. dec.

IR (Nujol): 3400, 1780, 1760, 1740, 1725, 1620 cm$^{-1}$

NMR (CD$_3$OD): δ=0.88 and 1.00 (2s, CH$_3$), 2.8 (3H), 5.85 (s, 1H) ppm.

TLC (CHCl$_3$—EtOH—NH$_4$OH 50/45/15) Rf=0.28.

EXAMPLE 13

Deoxy-3 N-(ε-L-lysyl) N'-acetylamino-3 digitoxigenin

3α isomer 385 mg of the 3α isomer obtained in Example 11 was hydrogenated in 40 ml of methanol in the presence of palladium at 5% on calcium carbonate for 2.5 hours. This was filtered and evaporated to dryness and the residue (282 mg) was crystallized in a mixture of propanol-2/ethyl acetate. This gave 212 mg of deoxy-3 N-(ε-(L)-lysyl) N'-acetylamino-3α digitoxigenin crystals, Compound C (yield=78%).

m.p. (Kofler) 195°-205° C. dec.

IR spectrum (Nujol): 3420, 1780, 1755, 1745, 1720 and 1615 cm$^{-1}$

TLC (CHCl$_3$—EtOH—NH$_4$OH 50/45/15) Rf=0.42.

(b) 3β isomer 420 mg of the 3β isomer obtained in Example 11 was hydrogenated in 50 ml of methanol, in the presence of 100 mg of palladium at 5% on calcium carbonate, for 3 hours. The residue (304 mg) was filtered, evaporated to dryness and crystallized in a mixture of methanol and ethyl acetate. This gave 211 mg of white deoxy-3 N-(ε-(L)-lysyl), N'-acetylamino-3β digitoxigenin crystals, Compound D (yield=74%).

m.p. (Kofler) 198°-205° C. dec.

IR spectrum (Nujol): 3460, 3280, 3040, 1800, 1755, 1745, 1735, 1720 and 1615 cm$^{-1}$ TLC (CHCl$_3$—EtOH—NH$_4$OH - 50/45/15) Rf=0.52.

EXAMPLE 14

Deoxy-3 ε-(α-N-benzyloxycarbonyl O-benzyl)-L-lysylamino-3 acetoxy-12β digoxigenin 1.5 g of oxo-3 acetoxy-12β digoxigenin and 2.92 g of α-N-benzyloxycarbonyl O-benzyl-L-lysine benzenesulfonate were dissolved in a solution of 100 ml of propanol-2. After 30 minutes under agitation at room temperature, 0.22 g of sodium borocyanohydride was added. After reacting for one night the major part of the solvent was distilled off and flooded in 100 ml of 1 N hydrochloric acid. After extraction of the acid fraction with ethyl acetate, washing the organic fractions with hydrochloric acid and then with water, the ethyl acetate was dried, and evaporated to dryness. The residue (1.65 g) was composed of amino acid, traces of amines and the starting material. The acid fractions were rendered alkaline to a pH 8-9 with concentrated ammonia and extracted with methylene chloride. After washing, drying and evaporating the organic extract to dryness, the residue (2.16 g) was composed of deoxy-3 ε-(α-N-benzyloxycarbonyl O-benzyl)-L-lysylamino-3β acetoxy-12β digoxigenin (yield=73%).

This residue was dissolved in 10 ml of methanol which was added drop by drop at reflux to a solution of 0.31 g of oxalic acid in solution in 10 ml of methanol at reflux. The residue was evaporated to dryness and crystallized in propanol-2, and then triturated in ether.

The crystals obtained (479 mg), after dissolving in water, rendering alkaline with ammonia, extraction with chloroform, drying and evaporating the extract to dryness, gave 422 mg of the least polar product, which was deoxy-3 ε-(α-N-benzyloxycarbonyl O-benzyl)-L-lysylamino-3β acetoxy-12β digoxigenin (yield=16%).

3β isomer m.p. (Kofler) oxalate=186°-194° C. dec.

IR spectrum (Nujol): 3430, 3250, 1780, 1755, 1730, 1635 and 1540 cm$^{-1}$

TLC CH$_2$Cl$_2$—MeOH (99/1, NH$_3$ atmosphere) Rf=0.50.

The third product mother liquors were evaporated to dryness and the base was liberated by rendering alkaline in suspension in dilute ammonia and extraction with chloroform. The residue was triturated in isopropyl ether. The solid insoluble material (720 mg) obtained was composed of deoxy-3 ε-(α-N-benzyloxycarbonyl O-benzyl)-L-lysylamino-3α acetoxy-12β digoxigenin (yield=25%).

3α isomer

IR (Nujol): 3420, 3300, 1780, 1735, 1620 and 1525 cm$^{-1}$.

TLC CH$_2$Cl$_2$—MeOH (99/1, NH$_3$ atmosphere) Rf=0.46.

EXAMPLE 15

Deoxy-3 ε-L-lysylamino-3 acetoxy-12b digoxigenin (a) 3α isomer 580 mg of the 3α isomer obtained in Example 14 was hydrogenated in 70 ml of methanol in the presence of 145 mg of palladium at 5% on calcium carbonate for 6 hours, and, after filtration, evaporation to dryness and crystallizing the residue (425 mg) in a mixture of methanol/ethyl acetate, 195 mg of deoxy-3 ε-L-lysylamino-3α acetoxy-12β digoxigenin crystals was obtained, Compound E (yield=46%).

m.p. (Kofler): 185°–195° C. dec.

IR spectrum (Nujol): 3400, 1780, 1755, 1745 and 1620 cm$^{-1}$

NMR spectrum (CD$_3$OD): δ=0.87 0.94 and 2.08 (3s, CH$_3$), 2.88 (3H), 3.6 (1H), 4.15 (1H), 5.85 (1H) ppm.

TLC (CHCl$_3$—EtOH—NH$_4$OH, 50/45/15 Rf=0.15.

(b) 3β isomer 325 mg of the 3β isomer obtained in Example 14 was hydrogenated in 40 ml of methanol in the presence of 80 mg of palladium at 5% on calcium carbonate for 4 hours, and, after filtration, evaporation to dryness and crystallizing the residue (238 mg) by washing with propanol-2 and trituration in ether, 154 mg of deoxy-3 ε-L-lysylamino-3β acetoxy-12β digoxigenin crystals was obtained, Compound F (yield=66%).

m.p. (Kofler) 180°–195° C. dec.

IR spectrum (Nujol): 3400, 1780, 1755, 1740 and 1620 cm$^{-1}$

NMR spectrum (CD$_3$OD): δ=0.85 0.98 and 2.10 (3s, CH$_3$), 2.82 (3H), 5.85 (s, 1H) ppm.

TLC CHCl$_3$—EtOH—NH$_4$OH - 50/45/15 Rf=0.25.

What is claimed is:

1. A process for the preparation of aminocardenolide derivatives represented by general formula (I):

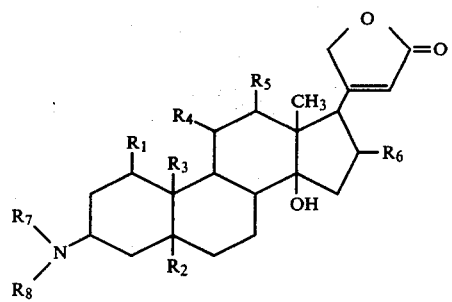

wherein $R_1$, $R_2$, $R_4$, $R_5$ and $R_6$, which may be the same or different, each represents a hydrogen atom or a hydroxy, alkoxy, or acyloxy group; $R_3$ represents a lower alkyl, hydroxyalkyl, acyloxyalkyl, haloalkyl or ethylenedioxyalkyl group; $R_7$ represents a hydrogen atom, or an alkyl or acyl group; and $R_8$ represents a hydrogen atom, an alkyl group or an amino acid residue, comprising reacting an oxo-3 genin with an ammonium salt in the presence of a borocyanohydride of an alkali metal in an organic solvent.

2. The process of claim 1, wherein the process includes adding the borocyanohydride to the oxo-3 genin and the ammonium salt in solution in said solvent and distilling the solvent off after the reaction.

3. The process of claims 1 or 2, wherein the ammonium salt is selected from the group consisting of ammonium acetate, methylamine hydrochloride, dimethylamine hydrochloride, a monoamino acid salt, a diamino acid salt, or an oligo-peptide amine salt.

4. The process of claims 1 or 2, wherein the reaction is carried out at room temperature, under agitation.

5. Alkylamino-3 cardenolide derivatives represented by general formula (II):

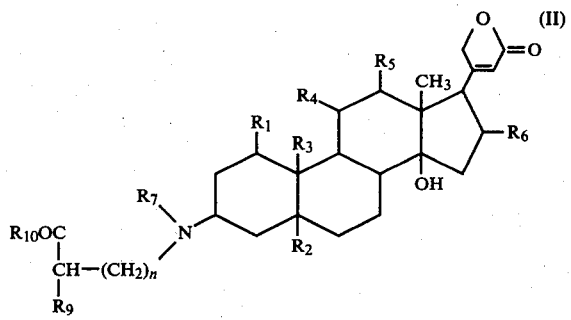

wherein $R_1$, $R_2$, $R_4$, $R_5$, and $R_6$, which may be the same or different, each represents a hydrogen atom or a hydroxy, alkoxy or acyloxy group; $R_3$ represents a lower alkyl, hydroxyalkyl, acyloxyalkyl, haloalkyl or ethylenedioxyalkyl group; $R_7$ represents a hydrogen atom, or an acyl or alkyl group; $R_9$ represents a hydrogen atom, an alkyl group or an —NR$_{11}$R$_{12}$ group; $R_{11}$ and $R_{12}$, which may be the same or different, each represents a hydrogen atom or an alkyl or aryloxycarbonyl group; $R_{10}$ represents a hydroxy, alkoxy, aryloxy or aralcoxycarbonyloxy group; and n is an integer from 0 to 6; and the base or mineral and organic acid salts thereof.

6. The alkylamino-3 cardenolide derivatives of claim 5, wherein $R_1$, $R_2$, and $R_6$ represent a hydrogen atom or a hydroxy group; $R_3$ represents a methyl or hydroxymethyl group, or an aldehyde group; $R_4$ represents a hydrogen atom; $R_5$ represents a hydrogen atom, a hydroxy group or an acetoxy group.

7. Alkylamino-3 cardenolide derivatives of claim 5 selected from the group consisting of:
deoxy-3 ε-L-lysylamino-3α digitoxigenin
deoxy-3 ε-L-lysylamino-3β digitoxigenin
deoxy-3 N-(ε-L-lysyl) N'-acetylamino-3α digitoxigenin
deoxy-3 N-(ε-L-lysyl) N'-acetylamino-3β digitoxigenin
deoxy-3 ε-L-lysylamino-3α acetoxy-12β digoxigenin
deoxy-3 ε-L-lysylamino-3β acetoxy-12β digoxigenin
deoxy-3 N-glycylamino-3α digitoxigenin deoxy-3 N-glycylamino-3β digitoxigenin.

8. A pharmaceutical composition comprising an alkylamino-3 cardenolide derivative of claims 5, 6 or 7 and a pharmaceutically acceptable carrier or diluent.

9. The process of claims 1 or 2 wherein $R_8$ is the group

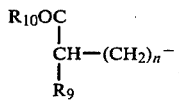

wherein $R_9$ represents a hydrogen atom, an alkyl group or an $-NR_{11}R_{12}$ group $R_{11}$ and $R_{12}$, which may be the same or different, each represents a hydrogen atom or an alkyl or aryloxycarbonyl group; $R_{10}$ represents a hydroxy, alkoxy, aryloxy or arylcoxycarbonyloxy group; and n is an integer from 0 to 6.

10. The process of claims 1, 2, or 9, wherein $R_3$ represents a lower alkyl, hydroxyalkyl, or an aldehyde group.

11. The process of claims 1, 2, or 9, wherein $R_3$ represents a lower alkyl or hydroxyalkyl group.

12. The process of claims 1, 2, or 9, wherein the solvent is an alcohol.

13. The process of claims 1, 2, or 9, wherein the solvent is an alcohol containing from 1 to 3 carbon atoms.

14. A pharmaceutical composition comprising an alkylamino-3 cardenolide according to claim 7 and a pharmaceutically acceptable carrier or diluent.

* * * * *